United States Patent
Ken et al.

(10) Patent No.: US 6,168,615 B1
(45) Date of Patent: Jan. 2, 2001

(54) METHOD AND APPARATUS FOR OCCLUSION AND REINFORCEMENT OF ANEURYSMS

(75) Inventors: Christopher G. M. Ken, San Mateo; David A. Ferrera, San Francisco, both of CA (US)

(73) Assignee: Micrus Corporation, Mountain View, CA (US)

( * ) Notice: Under 35 U.S.C. 154(b), the term of this patent shall be extended for 0 days.

(21) Appl. No.: 09/072,314

(22) Filed: May 4, 1998

(51) Int. Cl.$^7$ .............................. A61F 2/06; A61B 17/12; A61M 29/00
(52) U.S. Cl. .................................. 623/1; 623/11; 623/12
(58) Field of Search ....................................... 623/1, 11, 12

(56) References Cited

U.S. PATENT DOCUMENTS

| | | |
|---|---|---|
| 1,341,052 | 5/1920 | Gale . |
| 1,667,730 | 5/1928 | Green . |
| 2,078,182 | 4/1937 | MacFarland . |
| 2,549,335 | 4/1951 | Rahthus . |
| 3,334,629 | 8/1967 | Cohn . |
| 3,452,742 | 7/1969 | W.F. Muller . |
| 3,649,224 | 3/1972 | Anderson et al. . |
| 3,868,956 | 3/1975 | Alfidi et al. . |

(List continued on next page.)

FOREIGN PATENT DOCUMENTS

| | | |
|---|---|---|
| 4102550 A1 | 8/1991 | (DE) . |
| 0 183372 A1 | 6/1986 | (EP) . |
| 0 382014 A1 | 8/1990 | (EP) . |
| 0 747 014 | 12/1996 | (EP) . |
| 0 743 047 | 3/1997 | (EP) . |
| 0 820 726 A2 | 1/1998 | (EP) . |

(List continued on next page.)

OTHER PUBLICATIONS

Christos A. Athanasoulis, M.D. The New England Journal of Medicine, May 15, 1980 "Therapeutic Applications of Angiography" pp. 1117–1125 (1 of 2).
Christos A. Athanasoulis, M.D. The New England Journal of Medicine, May 22, 1980 "Therapeutic Applications of Angiography" pp. 1174–1179 (2 of 2).

(List continued on next page.)

Primary Examiner—Michael J. Milano
Assistant Examiner—Choon P. Koh
(74) Attorney, Agent, or Firm—Fulwider, Patton, Lee & Utecht, LLP

(57) ABSTRACT

The vasoocclusive apparatus can be used in a method of interventional therapy and vascular surgery by inserting the apparatus into a portion of a vasculature, for treatment of a body vessel such as an aneurysm in conjunction with a secondary vasoocclusive device to be placed within the vessel. The vasoocclusive apparatus includes a plurality of strut members connected together at a central hub that extend from a collapsed position to an expanded configuration to cross the neck of the aneurysm, dividing the neck into smaller openings, allowing the deployment of the secondary vasoocclusive device within the aneurysm but preventing migration of the secondary vasoocclusive device from the aneurysm. The strut members can be made from a twisted cable of strands of a superelastic material, such as a shape memory nickel titanium alloy, with at least one radiopaque strand. A shape memory collar is provided for detachably mounting the vasoocclusive apparatus to a pusher member and for detaching the vasoocclusive apparatus for deployment when a desired placement within an aneurysm to be treated and out of a parent vessel is achieved.

40 Claims, 2 Drawing Sheets

U.S. PATENT DOCUMENTS

| | | |
|---|---|---|
| 3,874,388 | 4/1975 | King et al. . |
| 4,007,743 | 2/1977 | Blake . |
| 4,494,531 | 1/1985 | Gianturco . |
| 4,512,338 | 4/1985 | Balko et al. . |

| Patent No. | Date | Name |
|---|---|---|
| 4,553,545 | 11/1995 | Maass et al. . |
| 4,619,246 | 10/1986 | Molgaard-Nielsen et al. . |
| 4,638,803 | 1/1987 | Rand . |
| 4,655,771 | 4/1987 | Wallsten . |
| 4,718,907 | 1/1988 | Karwoski et al. . |
| 4,748,986 | 6/1988 | Morrison et al. . |
| 4,768,507 | 9/1988 | Fischell et al. . |
| 4,795,458 | 1/1989 | Regan . |
| 4,800,882 | 1/1989 | Gianturco . |
| 4,813,925 | 3/1989 | Anderson, Jr. et al. . |
| 4,813,934 | 5/1992 | Engelson, et al. . |
| 4,820,298 | 4/1989 | Leveen et al. . |
| 4,830,003 | 5/1989 | Wolff et al. . |
| 4,850,960 | 7/1989 | Grayzel . |
| 4,856,516 | 8/1989 | Hillstead . |
| 4,950,258 | 8/1990 | Kawai . |
| 4,954,126 | 9/1990 | Wallsten . |
| 4,957,479 | 9/1990 | Roemer . |
| 4,957,501 | 9/1990 | Lahille et al. . |
| 4,990,155 | 2/1991 | Wilkoff . |
| 4,994,069 | 2/1991 | Ritchart et al. . |
| 5,026,377 | 6/1991 | Burton et al. . |
| 5,041,084 | 8/1991 | DeVries et al. . |
| 5,064,435 | 11/1991 | Porter . |
| 5,071,407 | 12/1991 | Termin et al. . |
| 5,104,404 | 4/1992 | Wolff . |
| 5,108,407 | 4/1992 | Geremia et al. . |
| 5,122,136 | 6/1992 | Guglielmi et al. . |
| 5,133,731 | 7/1992 | Butler et al. . |
| 5,133,732 | 7/1992 | Wiktor . |
| 5,133,733 | 7/1992 | Rasmussen et al. . |
| 5,141,502 | 8/1992 | Macaluso, Jr. . |
| 5,147,370 | 9/1992 | McNamara et al. . |
| 5,151,105 | 9/1992 | Kwan-Gett . |
| 5,160,341 | 11/1992 | Brenneman et al. . |
| 5,176,625 | 1/1993 | Brisson . |
| 5,176,661 | 1/1993 | Evard et al. . |
| 5,183,085 | 2/1993 | Timmermans . |
| 5,186,992 | 2/1993 | Kite, III . |
| 5,203,772 | 4/1993 | Hammerslag et al. . |
| 5,217,484 | 6/1993 | Marks . |
| 5,222,969 | 6/1993 | Gillis . |
| 5,226,911 | 7/1993 | Chee et al. . |
| 5,228,453 | 7/1993 | Sepetka . |
| 5,234,437 | 8/1993 | Sepetka . |
| 5,234,456 | 8/1993 | Silvestrini . |
| 5,243,996 | 9/1993 | Hall . |
| 5,250,071 | 10/1993 | Palermo . |
| 5,261,916 | 11/1993 | Engelson . |
| 5,304,194 | 4/1994 | Chee et al. . |
| 5,312,415 | 5/1994 | Palermo . |
| 5,336,205 | 8/1994 | Zenzen et al. . |
| 5,342,387 | 8/1994 | Summers . |
| 5,350,397 | 9/1994 | Palermo et al. . |
| 5,350,399 | 9/1994 | Erlebacher et al. . |
| 5,354,295 | 10/1994 | Guglelmi et al. . |
| 5,370,691 | 12/1994 | Samson . |
| 5,382,259 | 1/1995 | Phelps et al. . |
| 5,423,829 | 6/1995 | Pham et al. . |
| 5,423,849 | 6/1995 | Engelson et al. . |
| 5,425,744 | 6/1995 | Fagan et al. . |
| 5,433,727 | 7/1995 | Sideris . |
| 5,441,516 | 8/1995 | Wang et al. . |
| 5,443,478 | 8/1995 | Purdy . |
| 5,451,235 | 9/1995 | Lock et al. . |
| 5,507,767 | 4/1996 | Maeda et al. . |
| 5,514,176 | 5/1996 | Bosley, Jr. . |
| 5,522,822 | 6/1996 | Phelps et al. . |
| 5,522,836 | 6/1996 | Palermo . |
| 5,527,338 | 6/1996 | Purdy . |
| 5,540,680 | 7/1996 | Guglielmi et al. . |
| 5,549,624 | 8/1996 | Mirigian et al. . |
| 5,549,662 | 8/1996 | Cottone, Jr. . |
| 5,562,641 | 10/1996 | Flomenblit et al. . |
| 5,562,698 | 10/1996 | Parker . |
| 5,569,245 | 10/1996 | Guglielmi et al. . |
| 5,582,619 | 12/1996 | Ken . |
| 5,591,229 | 1/1997 | Parodi . |
| 5,593,422 | 1/1997 | Van de Moer et al. . |
| 5,601,600 | 2/1997 | Ton . |
| 5,607,445 | 3/1997 | Summers . |
| 5,624,461 | 4/1997 | Mariant . |
| 5,629,449 | 4/1997 | Pham et al. . |
| 5,637,113 | 6/1997 | Tartaglia et al. . |
| 5,639,277 | 6/1997 | Mariant et al. . |
| 5,643,254 | 7/1997 | Scheldrup et al. . |
| 5,645,558 | 7/1997 | Horton . |
| 5,649,949 | 7/1997 | Wallace et al. . |
| 5,667,522 | 9/1997 | Flomenblit et al. . |
| 5,669,905 | 9/1997 | Scheldrup et al. . |
| 5,669,931 | 9/1997 | Kupiecki et al. . |
| 5,676,697 | 10/1997 | McDonald . |
| 5,690,643 | 11/1997 | Wijay . |
| 5,690,666 | 11/1997 | Berenstein et al. . |
| 5,690,667 | 11/1997 | Gia . |
| 5,690,671 | 11/1997 | McGurk et al. . |
| 5,693,067 | 12/1997 | Purdy . |
| 5,700,258 | 12/1997 | Mirigian et al. . |
| 5,709,707 | 1/1998 | Lock et al. . |
| 5,718,711 | 2/1998 | Berenstein et al. . |
| 5,725,546 | 3/1998 | Samson . |
| 5,725,552 | 3/1998 | Kotula et al. . |
| 5,733,329 | 3/1998 | Wallace et al. . |
| 5,749,891 | 5/1998 | Ken et al. . |
| 5,749,894 | 5/1998 | Engelson . |
| 5,766,160 | 6/1998 | Samson et al. . |
| 5,776,219 | 6/1998 | Horton . |
| 5,782,909 | 7/1998 | Quiachon et al. . |
| 5,800,453 | 9/1998 | Gia . |
| 5,800,455 | 9/1998 | Palermo et al. . |
| 5,814,062 | 9/1998 | Sepetka . |
| 5,843,118 | 12/1998 | Sepetka et al. . |

FOREIGN PATENT DOCUMENTS

| | | |
|---|---|---|
| 592.182 | 7/1925 | (FR) . |
| 2 066 839 | 7/1981 | (GB) . |
| WO 94/09705 | 5/1994 | (WO) . |
| WO 94/10936 | 5/1994 | (WO) . |
| WO 97/26939 | 7/1997 | (WO) . |
| WO 97/31672 | 9/1997 | (WO) . |
| WO 97/48351 | 12/1997 | (WO) . |
| WO 99/05977 | 2/1999 | (WO) . |
| WO 99/07294 | 2/1999 | (WO) . |
| WO 99/29260 | 6/1999 | |

OTHER PUBLICATIONS

Alex Berenstein, M.D. and Irvin I. Kricheff, M.D. "Catheter and Material Selection for Transarterial Embolization: Technical Conderations" Radiology, Sep. 1979; pp. 631–639.

O.A. Battista, et al. Journal of Applied Polymer Science 1967 "Colloidal Macromolecular Phenomena. Part II. Novel Microcrystals of Polymers" pp. 481–498.

Sadek K. Hilal, M.D. et al. Journal of Neurological Surgery "Therapeutic Percutaneous Embolization for Extra–Axial Vascular Lesions of the Head, Neck and Spine" Sep., 1975; pp. 275–287.

Stephen L. Kaufman, M.D. et al. Investigative Radiology, May–Jun. 1978 "Transcatheter Embolization with Microfibrillar Collagen in Swine"; pp. 200–204.

Ashok J. Kumar, et al., Journal of Neuroradiology (1982) "Preoperative Embolization of Hypervascular Head and Neck Neoplasms Using Microfibrillar Collagen", pp. 163–168.

Richard E. Latchaw, M.D. et al., Radiology (1979) "Polyvinyl Foam Embolization of Vascular and Neoplastic Lesions of the Head, Neck and Spine" pp. 669–679.

Stewart R. Reuter, M.D. et al. American Journal of Radiology, Sep. 1975 "Selective Arterial Embolization for Control of Massive Upper Gastrointestinal Bleeding" pp. 119–126.

Glenn H. Roberson, et al., American Journal of Radiology, Oct. 1979 "Therapeutic Embolization of Juvenile Angiofibroma" pp. 657–663.

(WO) .

Sidney Wallace, M.D. et al., Cancer, Oct. 1979 "Arterial Occlusion of Pelvic Bone Tumors"; pp. 322–325 & 661–663.

"Mechanical Devices for Arterial Occlusion " by C. Gianturco, M.D., et al., Jul. 1975 pp. 428–435.

"Therapeutic Vascular Occlusion Utilizing Steel Coil Technique: Clinical Applications" by Sidney Wallace, et al., Am J. Roentgenol (1976); pp. 381–387.

"Transcatheter Intravascular Coil Occlusion of Experimental Arteriovenous Fistulas", by James H. Anderson, et al., Am. J. Roentgenol, Nov. 1977, pp. 795–798.

"'MINI' Gianturco Stainless Steel Coils for Transcatheter Vascular Occlusion" by James H. Anderson, et al., from the Department of Diagnostic Radiology at the University of Texas System Cancer Center, Aug. 1978, pp. 301–303.

"A New Improved Coil for Tapered–Tip Catheter for Arterial Occlusion" by Vincent P. Chuang, M.D., et al., May 1980, pp. 507–509.

International Search Report Dated Jun. 3, 1999.

"Neurosurgery interactive article part 2 –Clinical Studies Embolization of Cerebral Arteriovenous Malformations: part II–Aspects of Complications and Late Outcome" by Christopher Lundqvist, M.D., Ph.D., G.Wilkolm, M.D., Ph.D., 9/ 96, pp. 1–16.

"Shape Memory Alloys" by Jeff Perkins, pp. 1095–1096.

"Treatment of Large and Giant Fusiform Intracranial Aneurysms with Guglielmi Detachable Coils", by Y. Pierre Gobin, M.D., et al., J. Neurosurg., Jan. 1996, pp. 55–62. vol. 84.

"Endovascilar Treatment of Basilar Tip Aneurysms using Electrolytically Detachable Coils", by Cameron G. McDougall, M.D., et al., J. Neurosurg., Mar. 1996, pp. 393–399, vol. 84.

"Retrieval of Gugliemi Detachable Coil After Unraveling and Fracture: Case Report and Experimental results", by Scott C. Standard, M.D., et al., Neurosurgery, Nov. 1994, pp. 994–999, vol. 35, No. 5.

"Catheters, Embolic Agents Spark Neurointervention", by Gary Duckwiller, M.D., et al., Diagnostic Imaging, May 1994, pp. 66–70 & 102.

METHOD AND APPARATUS FOR OCCLUSION AND REINFORCEMENT OF ANEURYSMS

BACKGROUND OF THE INVENTION

1. Field of the Invention

This invention relates generally to implantable devices for interventional therapeutic treatment of defects in the vasculature, and more particularly concerns a detachable device having multiple strut members with collapsed and expanded configurations to be used in combination with a catheter for the occlusion and reinforcement of aneurysms.

2. Description of Related Art

Recently developed interventional procedures have been used to treat defects in the vasculature which are not easily reached by surgical procedures. More particularly, such interventional procedures have been developed to treat defects that are located in small and remote vessels such as those within the brain. During such interventional procedures, vasoocclusive devices are typically placed within the vasculature of the human body by use of a catheter, either to block the flow of blood through a vessel making up that portion of the vasculature through the formation of an embolus, or to form such an embolus within an aneurysm stemming from the vessel. Vasoocclusive devices used for these procedures can have a variety of configurations, and are generally formed of one or more elements that are larger in the deployed configuration than when they are within the delivery catheter prior to placement. One anatomically shaped vasoocclusive device that forms itself into a shape of an anatomical cavity such as an aneurysm is made of a preformed strand of flexible material such as a nickel-titanium alloy. One or more of such vasoocclusive members can be wound to form a generally spherical or oval shape in a relaxed, expanded state, and can be readily deformed to fit within a small diameter catheter from which they can be deployed at a treatment site.

Aneurysms have been treated with external surgically placed clips, or using vascular catheters, by detachable vasoocclusive balloons or an embolus generating vasoocclusive device such as one or more vasoocclusive coils. The delivery of such vasoocclusive devices can be accomplished by a variety of means, including via a catheter in which the device is pushed through an opening at the distal end of the catheter by a pusher to deploy the device. By using highly flexible materials for the vasoocclusive devices, the vasoocclusive devices can be produced in such a way that they will readily pass through the lumen of a catheter in a linear shape and take on a complex shape as originally formed after being deployed into the area of interest, such as an aneurysm.

One vasoocclusive device used to treat aneurysms is a tightly wound coil that is pushed into the aneurysm through the neck of the aneurysm so that the coil forms a complex shape with the aneurysm. When an embolus generating vasoocclusive device such as a vasoocclusive coil is used to treat an aneurysm, the success of the treatment depends upon whether the embolus generating vasoocclusive device can migrate out of the aneurysm through the neck of the aneurysm, which in turn is somewhat dependent upon whether the ratio of the diameter of the dome portion of the aneurysm to the diameter of the neck of the aneurysm is less than approximately 2:1. If the dome to neck ratio is larger than approximately 2:1, the possibility that the embolus generating vasoocclusive device will migrate out of the aneurysm into the parent vessel becomes greater, posing a risk to the success of the procedure.

It would, therefore, be desirable to provide a vasoocclusive device that can be used with or without a stent, coil or the like, that can be delivered to an aneurysm or other body vessel in a primary collapsed configuration, where the vasoocclusive device can be deployed and released to assume a secondary, expanded configuration which partially occludes the neck of the aneurysm and which also allows deployment of an additional embolus generating vasoocclusive device such as an embolic coil within the aneurysm, and blocks migration of the embolus generating vasoocclusive device from the aneurysm to the vessel. It would also be desirable to provide a device which offers the advantages of a shape memory alloy such as a nickel-titanium alloy, and that incorporates radiopaque material in a stable configuration that is not subject to fracture during use of the device, so that the device can be visualized under fluoroscopy. The present invention meets these and other needs.

SUMMARY OF THE INVENTION

One problem present in the treatment of saccular aneurysms by use of interventional therapy is presented when the aneurysm is formed such that the neck of the aneurysm is relatively large in at least one dimension compared to the maximum width of the dome of the aneurysm. In such a case, it is difficult to employ an embolus generating occluding device such as an embolic coil without raising the risk that the device will partially, or fully, deploy outside of the aneurysm and into the vessel, thereby presenting a risk to the patient.

The present invention provides for an improved method and apparatus which solves these and other problems by providing, in its broadest aspect, a partially occlusive vasoocclusive apparatus with a plurality of strut members that can be deployed in an expanded configuration across the neck of a body vessel such as an aneurysm, either alone, or to additionally allow deployment of a secondary vasoocclusive device or substance within the vessel, and to block migration of the secondary vasoocclusive device into the vessel. Specifically, with respect to the treatment of aneurysms, the vasoocclusive apparatus can be deployed across the neck of an aneurysm having a less than favorable dome to neck ratio to prevent migration of a secondarily placed embolus generating vasoocclusive device from the aneurysm.

Briefly, and in general terms, a presently preferred embodiment of the present invention provides for a vasoocclusive apparatus for use in interventional therapy and vascular surgery which is adapted to be inserted into a portion of a vasculature for treatment of a body vessel such as an aneurysm. The invention can be used in conjunction with secondary vasoocclusive devices such as embolic coils that can be placed within the aneurysm and partially retained by the apparatus. The vasoocclusive apparatus of the invention comprises a plurality of strut members or spokes extending from a central hub that can be deployed within an aneurysm, and that are radially extended in an expanded configuration to cross the neck of the aneurysm, dividing the neck into smaller openings, and thus allowing the deployment of the secondary vasoocclusive device by a catheter extending through the smaller openings in the invention within the aneurysm but preventing migration of the secondary vasoocclusive device from the aneurysm once it is deployed. In one presently preferred aspect of the invention, the device is made from a twisted cable of superelastic strands made of a suitable material, with the cable including at least one radiopaque strand, made of platinum, tungsten or gold, in order to serve as a marker during a procedure. In one presently preferred embodiment, the super-elastic material comprises a shape memory material such as nickel titanium alloy, that can be heat treated to remain superelastic or to have shape memory behavior such that the alloy is highly flexible at a temperature appropriate for introduction into the body via a catheter, and after placement, the device will take on a shape designed to optimize the therapeutic purposes desired for the device. In this regard, the disclosures of co-pending applications Ser. No. 08/986,004 filed Dec. 5, 1997 and Ser. No. 09/019, 841 filed Feb. 6, 1998 describe such radiopaque strands and three dimensional vasoocclusive devices formed therefrom, are incorporated by reference herein.

In a presently preferred configuration of the vasoocclusive apparatus, the plurality of strut members are connected together at a central hub, and extend radially from the central hub from a first collapsed configuration to an expanded configuration. The strut members can be arranged in a variety of configurations providing for a variety of occlusive properties. In a first preferred embodiment, the strut members are arrayed in a spiral configuration extending from the central hub. When the spiral strut members are configured, they may also be made so that they overlap at some point near their periphery in order to reinforce one another in the direction perpendicular to the strut, while retaining the resilience of the struts, so as to conform to the shape of the aneurysm opening. In a second preferred option, the strut members have curvilinear radial struts extending from the central hub. In a third preferred option, the strut members have an umbrella-like configuration of spokes extending from the central hub, the strut members additionally are crosslinked to adjacent strut members by cross-struts of shape memory material.

By use of the above configurations, and combinations of them, it can be seen that the openings in the device, represented by the areas between the struts, can be tailored to provide an area suitable for insertion of a placement catheter shaft to deploy embolic coils and the like within the aneurysm which will be held in place by the invention, thus preventing the embolic devices from entering the vessel and the resultant risk to the patient.

Similarly, the invention can allow for the deployment of other embolic agents within the aneurysm through the invention and lower or eliminate the migration of the embolic agent out of the aneurysm prior to being activated. In such a regard, it is specifically contemplated that the deployment of embolic agents such as polymers, glues, gels, micro-balloons and foams through openings in the device of the invention and into the aneurysm in which it is deployed, is contemplated as a preferred method in the use of this invention.

In another presently preferred aspect of the invention, mounting means are also provided for detachably mounting the vasoocclusive apparatus to a placement catheter shaft and for detaching the vasoocclusive apparatus for deployment when a desired placement within an aneurysm to be treated and out of a parent vessel is achieved. The mounting preferably comprises a collar of shape memory material disposed on one part of the vasoocclusive apparatus and mating with a distal portion of the placement catheter shaft and connecting the vasoocclusive apparatus and the placement catheter shaft. The shape memory collar can be heated to thereby assume a configuration disconnecting the vasoocclusive apparatus and the placement catheter shaft. In a currently preferred embodiment, the placement catheter shaft comprises a fiber optic compatible catheter shaft connected to an optical light source for conducting light energy to the collar to heat the collar and to thereby induce the collar to assume an enlarged configuration to detach the vasoocclusive device from the placement collar.

In a presently preferred embodiment of the method of using the invention, a device is formed which includes a plurality of flexible radial elements from a central hub, at least a portion of the radial elements being formed of a highly flexible material. The device is then deformed to fit within a placement catheter distally from a pusher element within the catheter. The catheter is then placed within the vasculature so that the distal opening of the catheter extends into an aneurysm or other deformation to be treated. The pusher is then used to expel the device into the aneurysm. In a presently preferred aspect of the invention, the pusher is an optional fiber which is coupled to the device by a shape memory material which can be heated by the energy transmitted through the optional fiber to cause the shape memory material to assume a shape which releases the device from the optional fiber. In other presently preferred embodiments, the device can be released by other means, such as thermo-mechanical, electromagnetic or disolution of an adhesive bond of the coupling between the device and the pusher.

The method of the invention for closing and occluding an opening of an aneurysm from a parent blood vessel accordingly thus comprises the steps of attaching an occlusive apparatus to the distal end of a linear pusher device, enclosing the pusher device and occlusive apparatus in a lumen of a catheter, with the pusher device proximal of the occlusive apparatus, positioning the catheter so that the distal opening of the catheter is in the opening between the aneurysm and the parent blood vessel, pushing the occlusive apparatus into the aneurysm by extending the pusher device towards the distal end of the catheter, and disconnecting the occlusive apparatus from the pusher device, thereby deploying the occlusive apparatus within the aneurysm and at least partially occluding the opening between the aneurysm and the parent blood vessel. In a presently preferred aspect of the method, the step of disconnecting the occlusive apparatus from the pusher device comprises causing energy to be transmitted through the pusher device to release the connection between the pusher device and the occlusive apparatus.

Advantageously, the method of the invention also provides for closing and occluding an opening of an aneurysm from a parent blood vessel, the steps of deploying a first occlusive apparatus within the aneurysm and at least partially occluding the opening between the aneurysm and the parent blood vessel; and deploying a secondary occlusive apparatus through said first occlusive apparatus within the aneurysm, whereby said first occlusive apparatus prevents migration of said secondary vasoocclusive device from the aneurysm into the parent blood vessel. The secondary occlusive apparatus can accordingly be deployed by the steps of attaching a secondary occlusive apparatus to the distal end of a linear pusher device; enclosing the pusher device and secondary occlusive apparatus in a lumen of a catheter, with the pusher device proximal of the secondary occlusive apparatus; positioning the catheter so that the distal opening of the catheter is in the opening between the aneurysm and the parent blood vessel; pushing the secondary occlusive apparatus into the aneurysm through the first occlusive apparatus by extending the pusher device towards the distal end of the catheter; and disconnecting the secondary occlusive apparatus from the pusher device, thereby deploying the secondary occlusive apparatus within the aneurysm, whereby the first occlusive apparatus prevents migration of the secondary vasoocclusive device from the aneurysm into the parent blood vessel.

DETAILED DESCRIPTION OF THE PREFERRED EMBODIMENTS

Figure 1:
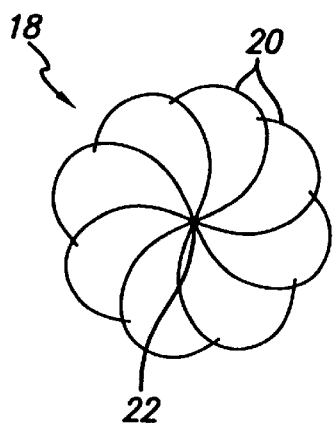
FIG. 1 is a top plan view of a first embodiment of a vasoocclusive apparatus according to the invention, having a spiral configuration of strut members shown in a primary collapsed configuration.

While an aneurysm can be treated by placement of an embolus-generating vasoocclusive device such as a vasoocclusive coil within the aneurysm, such an embolus-generating vasoocclusive device can migrate out of the aneurysm, particularly if the ratio of the diameter of the dome portion of the aneurysm to the diameter of the neck of the aneurysm is unfavorable, i.e., less than approximately 2:1, posing a risk to the success of the procedure.

As is illustrated in the drawings, which are provided for the purposes of illustration and not by way of limitation, the invention is embodied in a vasoocclusive apparatus adapted to be radially extended in an expanded configuration to cross the neck of a hollow body vessel such as an aneurysm, dividing the neck into a plurality of smaller openings 16 and thus to prevent migration of a secondary vasoocclusive device to be placed within the body vessel in conjunction with the vasoocclusive apparatus for treatment of the body vessel. According to the method of the invention, following deployment of the vasoocclusive apparatus within the body vessel, a secondary embolus-generating vasoocclusive device such as a vasoocclusive coil is deployed within the body vessel through the strut members. When the secondary vasoocclusive device assumes an expanded configuration, the vasoocclusive apparatus operates to prevent migration of the secondary vasoocclusive device from the aneurysm.

Figure 2:
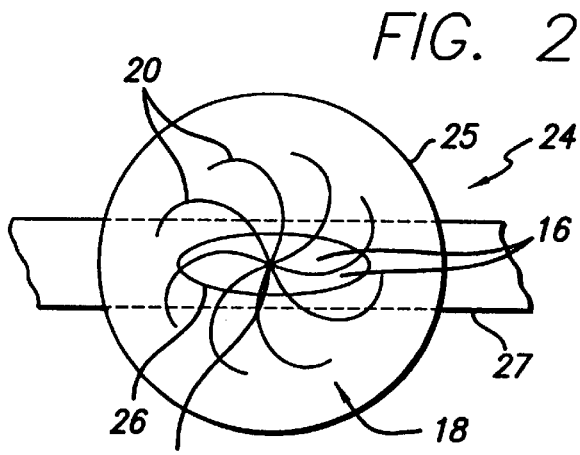
FIG. 2 is a top plan view of the vasoocclusive apparatus of FIG. 1, showing the spiral configuration of strut members in a secondary, expanded configuration within the dome of an aneurysm.
Figure 2A:
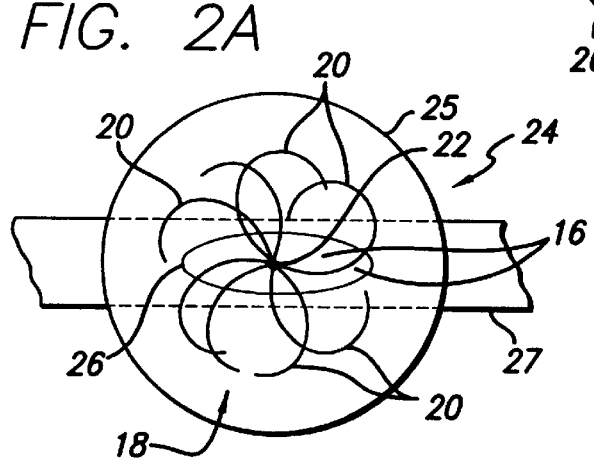
FIG. 2A is a top plan view of the vasoocclusive apparatus of FIG. 1, showing the spiral configuration of strut members in a an alternative randomly arranged secondary, expanded configuration within the dome of an aneurysm.
Figure 3:
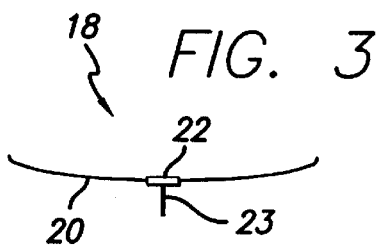
FIG. 3 is a side view of the vasoocclusive apparatus of FIG. 1, showing the spiral configuration of strut members in a primary, collapsed configuration.
Figure 4:
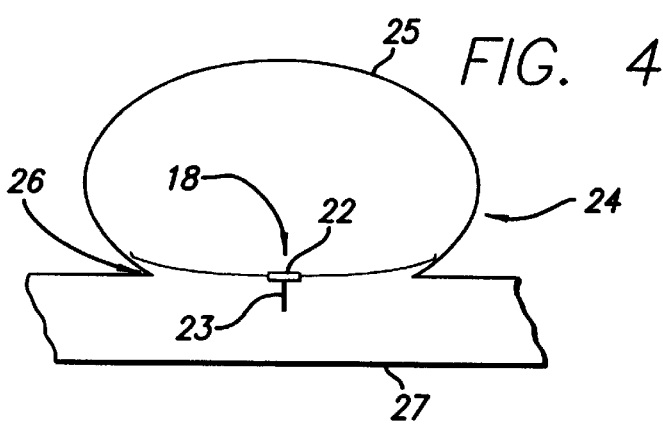
FIG. 4 a side view of the vasoocclusive apparatus of FIG. 2, showing the spiral configuration of strut members in a secondary, expanded configuration within the dome of an aneurysm.

With reference to FIGS. 1–4, the vasoocclusive apparatus 18 includes a plurality of strut members 20 connected together at a central hub 22, and extending radially from the central hub from a first collapsed configuration, illustrated for example in FIG. 1, to a corresponding expanded configuration such as is illustrated in FIGS. 2 and 4 within an aneurysm 24 having a dome portion 25, a neck portion 26, and a parent vessel 27. In a first preferred embodiment illustrated in FIGS. 1–4, the strut members are arrayed in a spiral configuration extending from the central hub. Alternatively, as is illustrated in FIG. 2A, the strut members can be arranged in a random or unsymmetrical configuration, extending from the central hub. In a presently preferred embodiment, the spiral struts are designed to overlap over at least a portion of their periphery to thereby reinforce one another at their periphery, while maintaining flexibility and conformability to the internal structure of the aneurysm. Extending from the central hub 22 can be a stem 23 used to attach the vasoocclusive apparatus to a pusher used to push the apparatus into the aneurysm and to detach the apparatus from the pusher after deployment.

Figure 5:
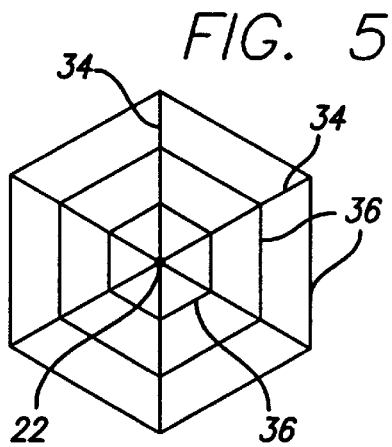
FIG. 5 is a top plan view of a fourth embodiment of a vasoocclusive apparatus according to the invention, having a web-like configuration of strut members, shown in a secondary, expanded configuration.

Referring to FIG. 5, the strut members 34 of the vasoocclusive apparatus have an umbrella-like configuration of spokes extending from the central hub 22, the strut members 34 of the vasoocclusive apparatus being additionally crosslinked to adjacent strut members by cross-struts 36 also formed of shape memory material. In this embodiment, the struts may also advantageously be of unequal length to allow the medical practitioners to chose a configuration of vasoocclusive device for specific desired shapes.

Figure 6:
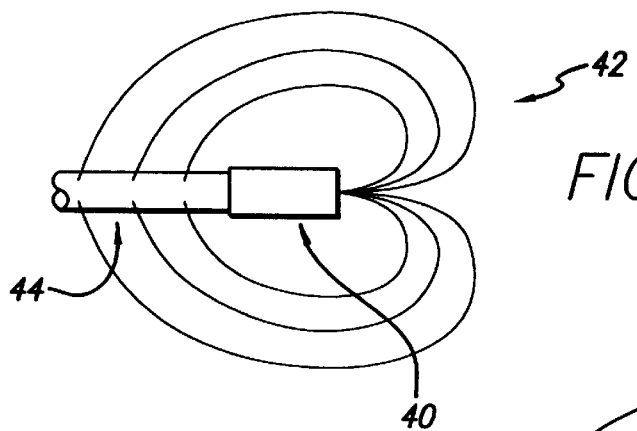
FIG. 6 is an illustration of a vasoocclusive apparatus of the invention attached to a placement catheter shaft, in a collapsed configuration ready for delivery for deployment within an aneurysm.
Figure 7:
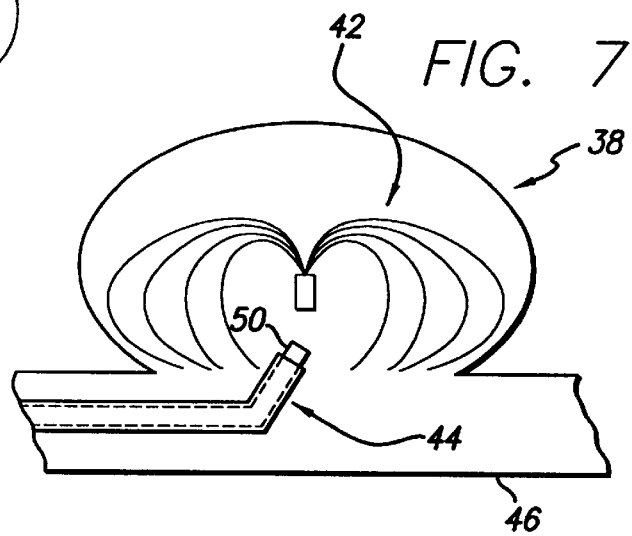
FIG. 7 is an illustration of a vasoocclusive apparatus of the invention attached to a placement catheter shaft, being deployed within an aneurysm.
Figure 8:
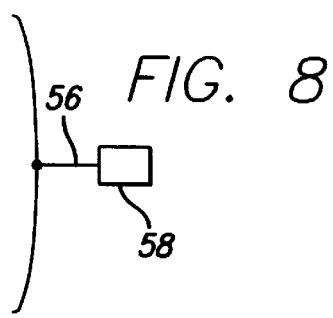
FIG. 8 is a side sectional view of a vasoocclusive apparatus of the invention attached to a placement catheter shaft showing a first embodiment of a means for mounting the vasoocclusive apparatus to the catheter shaft.
Figure 9:
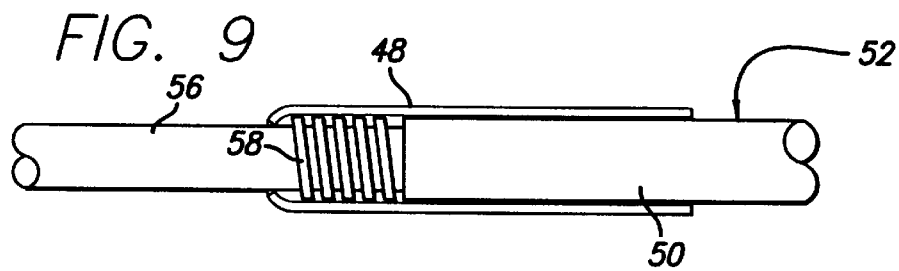
FIG. 9 is an exploded sectional view of a portion of FIG. 10, showing the connection of the vasoocclusive apparatus to the catheter shaft.

As is illustrated in FIGS. 6 and 7, each of the optional configurations of the strut members above are adapted to be deployed within an aneurysm 38, via a catheter in which the device is pushed through an opening at the distal end of the catheter by a pusher to deploy the device. Mounting means 40 are preferably provided for detachably mounting the vasoocclusive apparatus 42 and placement of the vasoocclusive apparatus via a placement catheter 44, and for detaching the vasoocclusive apparatus for deployment when a desired placement within an aneurysm 38 to be treated and out of a parent vessel 46 is achieved. Referring to FIGS. 8–11, the mounting means preferably comprises a shape memory collar 48 preferably formed of shape memory material and disposed on the vasoocclusive apparatus and a placement shaft of the pusher and connecting the vasoocclusive apparatus and the pusher shaft. FIGS. 6–8 illustrate an embodiment in which the collar is attached to the distal end 50 of a fiber optic pusher member 52 of the placement catheter 44. The shape memory collar is attached to the fiber optic pusher member by an adhesive which retains high strength at temperatures beyond the shape memory material transition point. In this embodiment of the mounting means, the central hub 54 of the vasoocclusive apparatus preferably includes a stem 56 to which a wire coil 58 is mechanically attached, although the wire coil could also be suitably soldered or welded to the stem. The shape memory collar is preferably heat treated in an unextended position illustrated in FIG. 8, and can be heated to a temperature that allows it to be worked and crimped into an extended position shown in FIG. 7 gripping over the end of the stem and wire coil to connect the vasoocclusive apparatus to the fiber optic pusher member of the placement catheter shaft.

Figure 10:
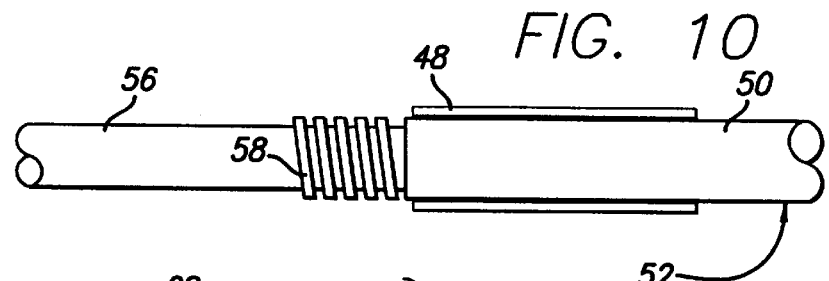
FIG. 10 is an exploded sectional view of a portion of FIG. 8, similar to that of FIG. 9, showing the release of the vasoocclusive apparatus from the catheter shaft.

When the vasoocclusive apparatus is delivered within the dome of an aneurysm as illustrated in FIG. 7, and when an operator is satisfied that the device is properly deployed, the shape memory collar can be heated, and thereby induced to shrink and pull back to assume a configuration shown in FIG. 10, disconnecting the vasoocclusive apparatus and the placement catheter shaft. The proximal end of the fiber optic catheter shaft (not shown) is preferably connected to an optical light source (not shown) for conducting light energy propagated at the distal end of the fiber optic pusher member to the shape memory collar and to thus heat the collar to return to its previous shape and induce the collar to detach the vasoocclusive device from the placement collar. Heating of the collar can at the same time heat the vasoocclusive apparatus to cause the vasoocclusive apparatus to expand within the aneurysm.

Figure 11:
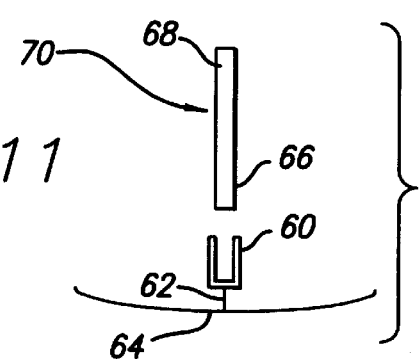
FIG. 11 is a side sectional view of a second embodiment of a means for mounting the vasoocclusive apparatus to the catheter shaft.

In an alternative embodiment of the mounting means illustrated in FIG. 11, the collar 60 can be disposed on the stem 62 of the central hub 64 of the vasoocclusive apparatus, adapted to be crimped to the distal end 66 of the fiber optic pusher member 68 of the placement catheter. In this embodiment, the distal end of the fiber optic pusher member of the catheter shaft optionally can have a surface defining a plurality of ridges and grooves 70 to aid in the connection of the collar to the fiber optic pusher member. Those skilled in the art will recognize that the invention can also be used with a variety of other placement catheter systems, and it is not intended that the invention be limited to the placement concepts illustrated by way of example.

It should be readily apparent that the delivery of the vasoocclusive devices of the invention can be accomplished by a variety of means. By using highly flexible materials for the vasoocclusive devices, the vasoocclusive devices can be produced in such a way that they will readily pass through the lumen of a catheter in a linear shape and take on a complex shape as originally formed after being deployed into the area of interest, such as an aneurysm.

In each of the foregoing embodiments, the strut members of the vasoocclusive device of the invention are preferably made from a twisted cable of superelastic strands made of a suitable material, with the cable including at least one radiopaque strand, made of platinum, tungsten or gold, in order to serve as a marker during the vascular surgical procedure. In a presently preferred aspect of the invention, the super-elastic material comprises a shape memory material such as nickel titanium alloy, that can be heat treated to remain superelastic or have shape memory behavior, such that the alloy is highly flexible at a temperature appropriate for introduction into the body via a catheter, and after placement, the device will take on a shape designed to optimize the therapeutic purposes desired for the device. In one presently preferred embodiment, the multi-stranded micro-cable from which the strut members are formed is approximately from 0.0021 to 0.006 inches in diameter, and comprises a plurality of flexible strands of nickel-titanium alloy, with at least one radiopaque wire which is approximately from 0.0007 to 0.002 inches in diameter. While the above stated diameters represent those presently known to be compatible with the invention, larger or smaller diameters may be useful for particular applications. The radiopaque wire can be formed of platinum or gold, for example, or other similar suitable radiopaque metals, in order to provide a radiopaque marker of the deployed configuration of a device made of the cable during vascular surgery.

While the invention is described in the context of shape memory metal materials, it is also contemplated that the invention could advantageously be made of other shape memory or superelastic materials, including shape memory plastics or superelastic metal alloys or plastics. Plastic materials may also more readily allow for the configuration of the invention in a variety of shapes and with simplified manufacturing, including molding of the vasoocclusive device, rather than fabrication from a number of component parts.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An occlusive apparatus for treatment of a body vessel, the vessel having a dome portion and a neck opening into another vessel, the apparatus comprising:
   a plurality of strut members centrally connected together that are adapted to be deployed within the vessel and that extend radially from a collapsed configuration to an expanded configuration to cross the neck of the vessel, dividing the neck into smaller openings.

2. The occlusive apparatus of claim 1, wherein said plurality of strut members are connected together at a central hub, and extend curvilinealy from the central hub from said first collapsed configuration to said expanded configuration.

3. The occlusive apparatus of claim 2, wherein said strut members are arrayed in a spiral configuration extending from said central hub.

4. The occlusive apparatus of claim 2, wherein said strut members have an umbrella-like configuration of spokes extending from the central hub.

5. The occlusive apparatus of claim 4, wherein said strut members additionally are crosslinked to adjacent strut members.

6. The occlusive apparatus of claim 2, wherein said strut members are randomly arranged.

7. The occlusive apparatus of claim 1, wherein said strut members are made from a twisted cable comprising strands of a superelastic material.

8. The occlusive apparatus of claim 7, wherein said cable further comprises at least one radiopaque strand of a metal selected from the group consisting of platinum, tungsten and gold.

9. The occlusive apparatus of claim 1, wherein said strut members are made from a twisted cable comprising strands of a shape memory nickel titanium alloy.

10. The occlusive apparatus of claim 9, wherein said strut members are heat treated to remain superelastic.

11. The occlusive apparatus of claim 9, wherein said strut members are heat treated to have shape memory behavior such that the alloy is highly flexible at a temperature appropriate for introduction into the body via a placement catheter, and after placement in the vessel, the apparatus will assume said expanded configuration.

12. The occlusive apparatus of claim 1, further comprising mounting means for detachably mounting the plurality of strut members to a placement catheter shaft and for detaching the plurality of strut members from the placement catheter shaft for deployment within the vessel to be treated.

13. The occlusive apparatus of claim 12, wherein said mounting means comprises a collar of shape memory material and said placement catheter shaft comprises a fiber optic pusher member, and wherein said collar is disposed on one of the occlusive apparatus and the fiber optic pusher member and connects the occlusive apparatus and the fiber optic pusher member.

14. The occlusive apparatus of claim 13, wherein said collar can be heated to be induced to assume a configuration disconnecting the occlusive apparatus and the fiber optic pusher member.

15. The occlusive apparatus of claim 14, wherein said fiber optic pusher member is connected to an optical light source for conducting coherent light energy to the collar to heat the collar to induce the collar to detach the occlusive device from the fiber optic pusher member.

16. The occlusive apparatus of claim 13, wherein said central hub comprises a stem having a proximal end adjacent to said strut members and a distal end, and further comprising a coil mechanically attached to the distal end of the stem.

17. The occlusive apparatus of claim 16, wherein the distal end of the fiber optic pusher member has a surface defining a plurality of ridges.

18. The occlusive apparatus of claim 1, wherein said apparatus is formed of a shape memory plastic material.

19. A vasoocclusive apparatus for treatment of an aneurysm in the vasculature in conjunction with a secondary vasoocclusive device to be placed within the aneurysm, the aneurysm having a dome portion and a neck opening into a parent vessel, the apparatus comprising:
    a plurality of strut members centrally connected together and having separate unconnected free ends adapted to be deployed within the aneurysm, said strut members extending radially from a collapsed configuration to an expanded configuration to cross the neck of the aneurysm, dividing the neck into smaller openings, allowing the deployment of the secondary vasoocclusive device within the aneurysm and preventing migration of the deployed secondary vasoocclusive device from the aneurysm into the parent vessel.

20. The vasoocclusive apparatus of claim 19, wherein said plurality of strut members are connected together at a central hub, and extend radially from the central hub from said first collapsed configuration to said expanded configuration.

21. The vasoocclusive apparatus of claim 20, wherein said strut members are arrayed in a spiral configuration extending from said central hub.

22. The vasoocclusive apparatus of claim 20, wherein said strut members have an umbrella-like configuration of spokes extending from the central hub, said strut members additionally are crosslinked to adjacent strut members.

23. The occlusive apparatus of claim 20, wherein said strut members are randomly arranged.

24. The vasoocclusive apparatus of claim 19, wherein said strut members are made from a twisted cable comprising strands of a superelastic material.

25. The vasoocclusive apparatus of claim 24, wherein said cable further comprises at least one radiopaque strand of a metal selected from the group consisting of platinum, tungsten and gold.

26. The vasoocclusive apparatus of claim 19, wherein said strut members are made from a twisted cable comprising strands of a shape memory nickel titanium alloy.

27. The occlusive apparatus of claim 26, wherein said strut members are heat treated to remain superelastic.

28. The occlusive apparatus of claim 26, wherein said strut members are heat treated to have shape memory behavior such that the alloy is highly flexible at a temperature appropriate for introduction into the body via a catheter, and after placement in the vessel, the apparatus will assume said expanded configuration.

29. The vasoocclusive apparatus of claim 19, further comprising mounting means for detachably mounting the plurality of strut members to a pusher member and for detaching the plurality of strut members from the pusher member for deployment within the vessel to be treated.

30. The vasoocclusive apparatus of claim 29, wherein said mounting means comprises a collar of shape memory material disposed on one of the vasoocclusive apparatus and the pusher member and connecting the vasoocclusive apparatus and the pusher member.

31. The vasoocclusive apparatus of claim 30, wherein said collar can be heated to be induced to assume a configuration disconnecting the occlusive apparatus and the pusher member.

32. The vasoocclusive apparatus of claim 31, wherein the pusher member comprises a fiber optic catheter shaft connected to an optical light source for conducting coherent light energy to the collar to heat the collar to induce the collar to detach the occlusive device from the fiber optic catheter shaft.

33. The vasoocclusive apparatus of claim 20, wherein said central hub comprises a stem having a proximal end adjacent to said strut members and a distal end, and further comprising a coil soldered to the distal end of the stem.

34. The vasoocclusive apparatus of claim 33, wherein the distal end of the fiber optic catheter shaft has a surface defining a plurality of ridges.

35. A method of closing and occluding an opening of an aneurysm from a parent blood vessel, comprising the steps of:
    attaching an occlusive apparatus having radial members extending from a central hub to the distal end of a linear pusher device;
    enclosing the pusher device and occlusive apparatus in a lumen of a catheter, with the pusher device proximal of the occlusive apparatus;
    positioning the catheter so that the distal opening of the catheter is in the opening between the aneurysm and the parent blood vessel;
    pushing the occlusive apparatus into the aneurysm by extending the pusher device towards the distal end of the catheter; and
    disconnecting the occlusive apparatus from the pusher device, thereby deploying the occlusive apparatus within the aneurysm and at least partially occluding the opening between the aneurysm and the parent blood vessel 36. The method of claim 35, wherein said step of disconnecting the occlusive apparatus from the pusher device comprises causing energy to be transmitted through the pusher device to release the connection between the pusher device and the occlusive apparatus.

37. The method of claim 35, further including the steps of:
    attaching a secondary occlusive apparatus to the distal end of a linear pusher device;
    enclosing the pusher device and secondary occlusive apparatus in a lumen of a catheter, with the pusher device proximal of the secondary occlusive apparatus;
    positioning the catheter so that the distal opening of the catheter is in the opening between the aneurysm and the parent blood vessel;
    pushing the secondary occlusive apparatus into the aneurysm through said first occlusive apparatus by extending the pusher device towards the distal end of the catheter; and disconnecting the secondary occlusive apparatus from the pusher device, thereby deploying the secondary occlusive apparatus within the aneurysm, whereby said first occlusive apparatus prevents migration of said secondary vasoocclusive device from the aneurysm into the parent blood vessel.

38. A method of closing and occluding an opening of an aneurysm from a parent blood vessel, comprising the steps of:

deploying a first occlusive apparatus within the aneurysm and at least partially occluding the opening between the aneurysm and the parent blood vessel; and deploying a secondary occlusive apparatus through said first occlusive apparatus within the aneurysm, whereby said first occlusive apparatus prevents migration of said secondary vasoocclusive device from the aneurysm into the parent blood vessel.

39. A method of closing and occluding an opening of an aneurysm from a parent blood vessel, comprising the steps of:

attaching a first occlusive apparatus having radial members extending from a central hub to the distal end of a linear pusher device;

enclosing the pusher device and first occlusive apparatus in a lumen of a catheter, with the pusher device proximal of the first occlusive apparatus;

positioning the catheter so that the distal opening of the catheter is in the opening between the aneurysm and the parent blood vessel;

pushing the first occlusive apparatus into the aneurysm by extending the pusher device towards the distal end of the catheter;

disconnecting the first occlusive apparatus from the pusher device, thereby deploying the first occlusive apparatus within the aneurysm and at least partially occluding the opening between the aneurysm and the parent blood vessel;

attaching a secondary occlusive apparatus to the distal end of a linear pusher device;

enclosing the pusher device and secondary occlusive apparatus in a lumen of a catheter, with the pusher device proximal of the secondary occlusive apparatus;

positioning the catheter so that the distal opening of the catheter is in the opening between the aneurysm and the parent blood vessel;

pushing the secondary occlusive apparatus into the aneurysm through said first occlusive apparatus by extending the pusher device towards the distal end of the catheter; and disconnecting the secondary occlusive apparatus from the pusher device, thereby deploying the secondary occlusive apparatus within the aneurysm, whereby said first occlusive apparatus prevents migration of said secondary vasoocclusive device from the aneurysm into the parent blood vessel.

40. The method of claim 39, wherein said step of disconnecting the first occlusive apparatus from the pusher device comprises causing energy to be transmitted through the pusher device to release the connection between the pusher device and the first occlusive apparatus.

* * * * *

UNITED STATES PATENT AND TRADEMARK OFFICE
CERTIFICATE OF CORRECTION

PATENT NO. : 6,168,615 B1
DATED : Jan. 2, 2001
INVENTOR(S) : Christopher G. M. Ken, David A. Ferrera It is certified that error appears in the above-identified patent and that said Letters Patent is hereby corrected as shown below:

Title page, page 2, first column, after "250,071" patent listing, add --5,258,042   11/1993   Mehta--.

Title page, page 2, second column, change "5,776,219", to read --5,766,219--.

Column 2, line 55, after "hub", add -- and having separate unconnected free ends--.

Column 8, line 24, claim 1, change "another", to read --the--.

Column 8, line 25, claim 1, after "together", add -- and having separate unconnected free ends--.

Signed and Sealed this

Twenty-ninth Day of May, 2001

Attest:

NICHOLAS P. GODICI

Attesting Officer

Acting Director of the United States Patent and Trademark Office